United States Patent [19]

Zmójdzin et al.

[11] 4,209,631
[45] Jun. 24, 1980

[54] PROCESS FOR THE SAFE NITRATION OF 2-METHYLIMIDAZOLE

[75] Inventors: Andrzej Zmójdzin; Kazimierz Urbański; Edmund Utecht; Władysław Stelmachowski, all of Poznań, Poland

[73] Assignee: Zaklady Chemiczne "Aspeta" Spoldzielnia Pracy., Pobiedziska, Poland

[21] Appl. No.: 375,857

[22] Filed: Jul. 2, 1973

[51] Int. Cl.² .......................................... C07D 233/92
[52] U.S. Cl. .................................................... 548/338
[58] Field of Search ......................... 260/309; 548/338

[56] References Cited

U.S. PATENT DOCUMENTS

| | | | |
|---|---|---|---|
| 3,417,091 | 12/1968 | Pickholz et al. | 260/288 |
| 3,631,060 | 12/1971 | Sklarz et al. | 260/309 |
| 3,634,446 | 1/1972 | Hoffer et al. | 260/309 |
| 3,666,644 | 5/1972 | Kollonitsch et al. | 204/158 HA |

FOREIGN PATENT DOCUMENTS 860953  2/1961  United Kingdom ..................... 260/688

OTHER PUBLICATIONS

Cosar et al., C.A. vol. 66: 2512x (1967).
Novikov et al., C.A. vol. 73: 66491z (1970).

Primary Examiner—Alan L. Rotman
Assistant Examiner—Richard A. Schwartz
Attorney, Agent, or Firm—Haseltine, Lake & Waters

[57] ABSTRACT

A method for the safe nitration of 2-methylimidazole with high output comprising nitrating the 2-methylimidazole with nitric acid and sulfuric acid as nitrating agents to produce 2-methyl-5-nitroimidazole, and controlling the reaction by adding as an inhibitor the reaction product itself or an excess of the concentrated nitric acid. The reaction can be carried out in stages with a reduced temperature in the first stage and an increased temperature in a subsequent stage.

2 Claims, No Drawings

PROCESS FOR THE SAFE NITRATION OF 2-METHYLIMIDAZOLE

BACKGROUND (a) Field of the Invention

This invention relates to a process for the nitration of 2-methylimidazole by means of nitric and sulphuric acid, assuring full safety and high output, notwithstanding the rapid and intensive course of the reaction as well as the use of high concentrated acid solutions.

(b) Prior Art

It is very difficult to introduce the nitric group into the imidazole ring because this requires the employment of extremely intense conditions, i.e. high temperature as well as high excesses of concentrated acids, such as nitric and sulphuric acid. This reaction is accompanied with a very intensive development of nitrogen oxides and a very high exothermic effect coupled with a splitting of part of the 2-methylimidazole and a full oxidation of the split products. By such conditions, the completion of this process, which runs effectively on the edge of a nitration and a splitting producing great quantities of energy, is indeed difficult, since at each moment any uncontrolled, violent reaction can occur what can lead to an explosion.

As industrial conditions for carrying out this reaction it is fundamentally necessary to provide assurance of complete safety, and therefore when employing known processes for the nitration of 2-methylimidazole, special methods of proceeding have been used. These consisted of first forming the solution of the 2-methylimidazole in sulphuric acid with the formation of an acid sulfate of the 2-methylimidazole.

This solution has been added in small portions or dropped very slowly into the nitrating mixture in order to have in the reacting solution only small quantities of 2-methylimidazole or to assure a full reaction before the introduction of each new portion. There were also employed reverse methods consisting in a slow and gradual introduction of nitrates or of nitric acid into the solution of 2-methylimidazole in sulphuric acid. In any event, the principle of such a processing is to keep in the solution during the nitration only small quantities of one of the reacting agents, i.e. of the organic substance or of the eventual oxidizer. Such a method could be used under industrial conditions, but the slow operation of this process considerably increases the processing costs and notwithstanding these safety measures, there is still no guaranty of a safe course of the reaction and there have occurred accidents and even explosions. It has been found through research, that the cause of these accidents was that in the presently used processes, the nitration of the sulphate of 2-methylimidazole does not start at once after the introduction of the reagents, but requires an induction time, which unfortunately is variable and difficult to be predicted. Owing to this, when reagents are continuously added, they can accumulate in the solution and cause an explosion. The velocity of the reaction after the induction period indeed increases very quickly by producing a violent exothermic effect and the induction agents, which start the reaction, were unknown. Moreover, in the known methods, the output was generally relatively low, taking into consideration the great inconvenience caused by the necessity of applying special conditions during the operation of the process, and under the best conditions the output is only 48–52%.

Better results are obtainable by the known Pyman method, but this unfortunately is only suitable on a laboratory scale. This method consists of the nitration of very small portions, on the order of several grams of 2-methylimidazole, which were previously dissolved in nitric acid to yield the nitrate of this compound. To such a prepared compound, sulphuric acid was added; after a short period of time a rapid increase of temperature occurred and a violent reaction started, which by reason of the small quantities of reagents introduced in the reaction was not so dangerous. Because of such "microexplosions" it was possible to treat only small portions of this compound, but the use of this method on an industrial basis proved to be impossible. This method however obtained an output of 63% of theoretical.

Owing to the great demand for 2-methyl-5-nitroimidazole, a compound used as raw material in the chemical and pharmaceutical industry, it has been also proposed to make the nitration process of the 2-methylimidazole safer by employing, during the reaction, deterrents, i.e. neutral substances, which not only do not take active part in the nitration process, but dilute the reaction mixture and increase the mass and the thermal capacity of the system, which reduces the sensitivity of the mixture and the possibility of explosion, and in any event it reduces its energy.

Hence, according to USSR patent specification No. 20247, it was proposed to use a deterrent, an additional product introduced into the mixture, such as sodium sulphate with sulphuric acid or an aqueous solution of acid sodium sulphate.

In the process described in German Pat. No. DBP-1.808.104 and French Pat. No. 2.022.956 it has been proposed to use as deterrents, carbamide and sulphuric acid or carbamide sulphate. The addition of the deterrent has rendered the operation of the reaction safer, but a serious disadvantage of this is the introduction of supplementary raw materials and the necessity of an important increase of nitrating acids already used in very high quantities, whereby owing to the dilution of the reaction product it was moreover necessary to carry out a troublesome process of isolating the reaction product from the large volume of the reaction mixture. Furthermore, the presence of foreign products made the following treatment very difficult, particularly the cleaning of the 2-methyl-5-nitroimidazole, which considerably increased the costs of production of this compound.

SUMMARY OF THE INVENTION

The invention relates to a method which avoids all these inconveniences, and particularly it provides a process, which can be carried out on an industrial scale and in which maximum security is effected by simultaneous avoidance of the use of undesired foreign substances and by a considerable reduction of the use of acids, with considerable acceleration of the course of the technological process as well as considerable increase of output.

According to the invention it has been found, that a suitable and perfect deterrent is the reaction product itself which is obtained in the nitration reaction of the 2-methylimidazole, which can also be added to the reacting mixture in order to reduce the reaction velocity, e.g. when it proceeds towards violent reaction. The addition of such a deterrent not only improves the safety conditions of the process but, moreover, enables a substantial reduction of the course of the technological process, whereby great volumes of neutral substances are avoided as well as the necessity of their removal from the mixture, which would increase the cost of operation. Moreover, the addition of the deterrent according to this invention accelerates the induction period of the reaction.

Further, according to this invention, it has been determined that the addition of concentrated nitric acid to the reaction mixture, despite expectations, produces a braking or inhibiting effect on the running nitrating reaction. This enables the use of a complexity of means, which ensure a safe control of the course of the reaction, its moderation by addition of nitric acid or its acceleration or its maintaining by gradual addition of sulphuric acid, this being particularly important when initial portions of reacted nitrated solutions, which contain 2-methyl-5-nitroimidazole, are to be produced and may be used as a deterrent for treating the next production batch.

According to the invention it has been further determined, that the reaction period can be substantially reduced while maintaining full safety, when the process is conducted at varying temperatures, whereby simultaneously during the course of the nitrating reaction, performed substantially at temperatures up to 110° C., the developing vapors and gases are condensed and recycled to the reaction medium, and then, preferably after addition of all reagents and a substantial diminishing of the reaction velocity and of the exothermic effect, the reaction is completed by raising the temperature to 130°–150° C. for a certain period, whereby the nitrated mixture is condensed and the volatile components developing at this time are distilled off.

Furthermore, it has been unexpectedly learned, that even better results, especially a further increase of output, can be obtained by means of developing this principle, namely by conducting this reaction from the beginning in stages at various temperature levels whereby the reaction is initially started in a temperature range of 60°–90° C., preferably 80°–90° C., and then gradually or continuously raising the temperature, preferably up to 110° C. after addition of all reagents, and at the same time the vapors and gases are condensed then after a substantial diminishing of the reaction velocity and of the exothermic effect, the process is completed by raising the temperature to 130°–150° C. for a suitable period, whereby at the same time that the nitrated mixture is condensed the developing volatile constituents are distilled off.

It has also been unexpectedly found, that better results, particularly a further increase of output can be obtained when this principle is further elaborated, i.e. by conducting the reaction from the beginning at a temperature between 60°–90° C., preferably 80°–90° C., and then raising the temperature gradually and continuously, preferably after addition of all reagents only, up to 110° C. with simultaneous condensing of the vapors, and only after the fundamental reaction has ended a condensation is effected by distillation of the volatile components at a temperature from 130°–150° C.

It has been also unexpectedly found, that it is possible to avoid the use of large quantities of acids, by using high concentrated nitric acid, such as of 1.47–1.52 density. Employing such an acid for the reaction according to this invention, it is possible to use a far smaller quantity of reagents, and particularly it is possible to reduce the amount of the sulphuric acid. Moreover, there are produced solutions with a higher content of 2-methylimidazole.

The process according to this invention permits the nitration of 2-methylimidazole under substantially safe conditions and with high yield of about 63–66%. Further improvements make possible a substantial reduction of the reaction time and an increase of the treating ability as well as a further increase of the output by about 5% to heretofore unattainable level of 70% of the theoretical. The process according to this invention also enables a radical decrease in the amount of the acids used while obtaining high concentrated solutions of 2-methyl-5-nitroimidazole. This is not only advantageous for the further treatment, but it makes possible a substantial reduction of the quantity of waste water and of auxiliary raw materials, such as, ammonia water and the like, as was heretofore necessary for the neutralization of the reaction mixture used in further treatments.

These further improvements may be used separately or jointly in the process according to this invention, each of which assures particular technical and technological advantages.

In the method according to this invention, a solution of 2-methylimidazole from a previously reacted solution of a foregoing production batch was separated and thereinto was introduced the entire quantity of nitric acid and a gradual addition of sulphuric acid until the start of an exothermic reaction by which the nitrate of 2-methylimidazole contained in the solution is transformed into 2-methy-5-nitroimidazole, whereby the conduct of this reaction and its velocity is controlled by gradual introduction of sulphuric acid as an accelerating agent, or if necessary of previously reacted solution or of pure nitric acid as inhibitors. By such a method of carrying out this process, according to the invention, it is possible to employ at the same time all further improvements and thereby assure a cumulation of technical and technological advantages.

DETAILED DESCRIPTION

The nitration reaction of the 2-methylimidazole according to this invention, under safe technological conditions and with high output and further advantages, are next described in the following Examples in which all the temperatures are given in Celsius degrees.

EXAMPLE I

In an enamel vessel of 75 liters capacity, provided with a mixer and a cooling mantle, 10 liters of nitric acid with a density of 1.40 were introduced and there were added 5 kg of 2-methylimidazole by continuous stirring and cooling in such a manner, that the temperature did not exceed 60°. Then 10 liters of sulphuric acid with a density of 1.84 were added to the solution such that the temperature was not greater than 110°. The reaction gradually began to start, by a violent boiling of the solution and liberation of brown fumes. For control of the reaction velocity there were gradually added to the mixture 6 additional liters of nitric acid so, that the temperature was kept at a constant level. In the case of an excessive inhibition of the reaction course, its further operation was regulated by addition of sulphuric acid, which was introduced gradually in a total amount of 6 liters when the intensity of the reaction began to diminish. After all the reagents have been added, the solution was continued to be stirred until the full completion of the reaction and the decline of the exothermic effect, with corresponding reduction and then elimination of cooling. The solution was left to stand to cool, was diluted with 40 liters of water and neutralized with ammonia liquor to a pH of 6. A bright yellow or almost white precipitate of 2-methyl-5-nitroimidazole was filtered, washed by means of small portions of water and dried to obtain 4.640 Kg of final clean product, representing a yield of about 61% output of theoretical.

EXAMPLE II

Into a boiler made of acid-resistant stainless steel of 250 liters capacity, provided with a mixer and a cooling jacket, there was introduced a reaction solution, such as that obtained in example I, and while cooling and stirring 15 kg of 2-methylimidazone was dissolved therein in a manner such that the temperature did not exceed 60°. Then 50 liters of nitric acid of 1.40 density were added and sulphuric acid of 1.84 density was gradually introduced, whereby an intensive reaction with liberation of nitric oxides started at once and the temperature increased to 110°. The temperature was maintained at this level by cooling and mixing and then as the reaction began to cease and the exothermic effect to diminish, sulphuric acid was gradually added in small portions such that the temperature was maintained at a constant level until a total quantity of 50 liters of the acid was added. After complete reaction and cooling of the solution, ¼ of the entire amount was left for the treatment of the next charge and from the remaining part 14.1 kg of 2-methyl-5-nitroimidazole were obtained in conventional manner corresponding to an output of about 61% of theoretical.

EXAMPLE III

In a glass flask of 15 liters capacity, provided with a reflux condenser, 6 liters of nitric acid of a density of 1.40 were placed and 2 kg of 2-methylimidazole were placed and 2 kg of 2-methylimidazole were added with cooling and stirring so that the temperature did not exceed 60°. Then sulphuric acid of a density of 1.84 was gradually added until the start of an intensive reaction with simultaneous liberation of nitric oxides and increase of the temperature to about 110° at which time the addition of the sulphuric acid was interrupted, and by intensive cooling, as well as addition of nitric acid, further increase of the reaction speed was inhibited and the temperature maintained at 110°.

After several minutes, when the intensity of the reaction began to lessen, there was gradually introduced 5 liters of sulphuric acid until the entire amount of 5 liters was exhausted and after the fundamental reaction finished, which lasted about 55 minutes, the flask was opened and a single portion of 1 liter of sulphuric acid was added to cause a rapid growth of the temperature to about 150° and a violent boiling of the solution for about 5 minutes. After cooling, there was obtained in conventional manner 1.990 kg of product corresponding to an output of about 66% of theoretical.

Following this process in a similar way, but by employing the reflux condenser during the entire time of running of this reaction and by maintaining the same at a constant temperature, 1.870 kg of product were obtained, whereby the volume of the solution as well as of ammonia liquor necessary to eliminate 2-methyl-5-nitroimidazole were far greater.

EXAMPLE IV

Into a vessel made of acid-resistant stainless steel of 75 liters capacity, provided with a stirring device and a cooling jacket, a nitrated solution, obtained as in examples I or III, was placed and 6 kg of 2-methylimidazole were gradually introduced, while cooling and stirring, and then 20 liters of nitric acid of 1.40 density were introduced such that the temperature does not exceed 70°. The vessel was closed and connected by a valved conduit to an absorption device, provided with a cooled receiver. Sulphuric acid was gradually introduced until an increase of the temperature to 100° and the start of an intensive reaction was noted, this being associated with the eliminating of great quantities of nitric oxides. The addition of sulphuric acid was interrupted and the temperature maintained at 110°, by intensive cooling and periodic addition of condensates from the receiver, and to initially inhibit the reaction there is added in the first stage 1 liter of nitric acid of a density of 1.40. After stabilization of the reaction speed, a further uniform course of the reaction was maintained by gradual introduction of sulphuric acid to the use of a total amount of 20 liters, by simultaneously periodically filling up the nitrating vessel with the content of the receiver, when the reaction tended to become more violent. After the intensity of the reaction declined, which lasted about 1 hour, the cooling was interrupted and after five minutes the temperature gradually raised to about 140° and a fulfillment of the reaction at this temperature effected until the decline of the exothermic effect, at which time the solution was evaporated and condensed and the volatile components, which were liberated during this period, such as gases and vapors, have not been recycled to the reaction medium. After cooling of the reacted mixture, ¼ of the volume of the solution was retained for treatment in the same way with the following charge and from the remaining quantity, after neutralization with ammonia, there were obtained 5.820 kg of 2-methyl-5-nitroimidazole corresponding to an output of about 64% of theoretical.

EXAMPLE V

In a nitrator made of acid-resistant stainless steel of 75 liters capacity, provided with a reflux condenser, a mixer and a thermometer as well as a cooling mantle, there were dissolved 8 kg of 2-methylimidazole into a solution already nitrated as in example IV, and then 24 liters of nitric acid of 1.40 density were added in such a manner, that the temperature was maintained at 70°. Thereafter sulphuric acid of 1.84 density was added such that, by simultaneous stirring and cooling, a constant temperature was maintained. After addition of 10 liters of sulphuric acid, the introduction was interrupted and after 10 minutes the sulphuric acid was gradually introduced until a total quantity of 24 liters was used. The reaction proceeded progressively more intensively and the flow of cooling water was correspondingly increased. A supplementary reservoir in the form of a tank with a conduit enabled the introduction of 10 liters of already reacted nitrated solution to the nitrator—a similar device was used in all reactions which have begun at a low temperature. During and after addition of the entire quantity of sulphuric acid, the solution was continually stirred and cooled for 15 minutes, and then, after a clear diminution of the reaction and diminishing of the exothermic effect, a slow increase of temperature, degree by degree in one minute, was allowed until a temperature of 110° has been reached. The mixture was maintained at this temperature for 15 minutes more. Then the reflux condenser was disengaged, while simultaneously leading the liberated vapors and gases directly to the absorption device, and the flow of the cooling water was terminated. The temperature of the reacting mixture raised by itself, reaching at the end a temperature of 138°. At this temperature the reaction was completed in 20 minutes, whereby the solution was condensed by distilling off about 3 liters, mainly water and nitric acid (i.e. diluted nitric acid), whereby after this treatment the cooling of the mixture was reinstituted. In the nitrator, 20% of the volume of the solution was retained for the treatment of the following charge, and from the remaining quantity there was obtained in known manner 8.700 kg of 2-methyl-5-nitroimidazole corresponding to 70% of theoretical.

EXAMPLE VI

Into a glass bottle of 750 ml, provided with a reflux condenser, 50 g of 2-methylimidazole was placed and while constantly stirring and cooling, 10 ml of sulphuric acid of 1.84 density were carefully and gradually introduced in such a way, that the temperature did not exceed 120° (2-methylimidazole is a free base and its transformation into the sulphate of 2-methylimidazole is a highly exothermic reaction). Then there was slowly introduced 20 ml of sulphuric acid and after lowering the temperature to about 50°, 100 ml of nitric acid with a density of 1.50 was poured in, and, if a too violent course of the reaction in the first stage was detected, the reaction could be inhibited by addition of several ml of nitric acid of 1.50 density. Then, after several minutes, as the intensity of the reaction and of the exothermic effect began to diminish sulphuric acid was added up to exhaustion of the entire quantity of 50 ml. After the sulphuric acid was added, the reflux condenser was removed and the temperature raised to 130°-150°. The solution remained for complete cooling and in a known manner, by means of neutralization with ammonia water, 4.5 g of 2-methyl-5-nitroimidazole were isolated corresponding to a yield of about 60% of theoretical.

EXAMPLE VII

In a bottle of 1 liter capacity, an untreated mixture obtained by nitration of the 2-methylimidazole as in examples I, III and V were placed and while stirring and mixing, 100 g of 2-methylimidazole were dissolved in such a manner, that the temperature did not exceed 70°. Then a reflux-condenser was connected and 200 ml of nitric acid of a density of about 1.50 were added, and thereafter sulphuric acid of 1.84 density was gradually introduced such that the temperature increased to 110°. The reaction, which started at once without delay, was intensive with violent liberation of nitric oxides. Then as the intensity of the reaction declined, further quantities of sulphuric acid were added until exhaustion of a quantity of 100 ml, and after the exothermic effect diminished the reflux condenser was changed to a normal one, whereby the temperature of the mixture increased to about 140° by simultaneous distilling off several ml of volatile components. After the reaction the solution was divided, and ⅓ remained for the treatment in the same way as the following charge and from the remaining ⅔ of the solution there were isolated 98 g of 2-methyl-5-nitroimidazole corresponding to about 66% of theoretical.

EXAMPLE VIII

Into a nitrator of 900 liters capacity, made of acid-resistant stainless steel and provided with a stirring device, a cooling jacket and an exhauster connected with an absorption device with a built-in receiver, which was provided with an outlet connected with the nitrator, there were introduced 110 liters of a nitrated solution, obtained by nitration of 2-methylimidazole as in example I, and then 75 kg of 2-methylimidazole was dissolved into this solution, while cooling and stirring the same, so that the temperature did not exceed 80° and at the end of the reaction it reduced to 40°. Then 150 liters of nitric acid of 1.50 density were added whereby the temperature increased to 80°, and then sulphuric acid of 1.84 density was gradually added so that the temperature increased gradually to about 100° and then remained at this level. During the addition of the sulphuric acid, the condensate was from time to time removed from the receiver, particularly at moments when the reaction began to become more violent. After addition of the entire quantity of sulphuric acid (about 70 liters) and a clear diminishing of the exothermic effect was noted, the temperature of the mixture was raised to about 140° and after 20 minutes (total reaction time was about 80 minutes) the solution was cooled, 110.1 of the solution was left in the nitrator for further nitration of the next charge and from the remaining quantity 75 kg of 2-methyl-5-nitroimidazole was obtained by neutralization of the reaction mixture with ammonia in a conventional manner.

EXAMPLE IX

In a boiler of acid-resistant stainless steel of 800 liters capacity, provided with a stirring device, a cooling jacket and an efficient reflux condenser, 150 liters of nitric acid of 1.50 density preheated to about 85° was placed and stirred in order to maintain a constant temperature and a nitrated solution obtained as in example I was poured in dropwise and then 80 kg of 2-methylimidazole in 80 liters of concentrated sulphuric acid was added. The reacting solution was stirred until a clear diminishing of the exothermic effect was noted and the temperature was raised gradually, after 1 hour, to 110° and this temperature was maintained for 25 minutes. The reflux condenser was thereafter removed and the temperature increased to about 140° and was maintained at this level for 30-minutes, the volatile components being distilled off during that time and removed from the reacting medium. The reacted solution was cooled and divided, and ⅓ was left in the nitrator, and from the remaining ⅔ of this solution 2-methyl-5-nitroimidazole was isolated in known manner (by diluting with water and neutralizing with ammonia to pH about 6). 88 kg of product were obtained corresponding to about 77% of theoretical.

EXAMPLE X

In a nitrated solution obtained as in example VIII 75 kg of 2-methylimidazole was dissolved with simultaneous mixing and cooling. The reflux condenser was connected and 120 liters of nitric acid of 1.50 density poured in, whereafter sulphuric acid was gradually added so that by simultaneous stirring and cooling, a constant temperature of 80° was maintained. 15 minutes after addition of all the reagents, a gradual increase of temperature, 10° in each 15 minutes, was noted until a temperature of 110° was reached. The solution was maintained at that temperature for 20 minutes and thereafter the reflux condenser was disconnected and the temperature of the reacting mixture increased to about 140°, whereby the volatile components were distilled from the reaction medium. ¼ of the solution was left for treatment in a similar way for the following charge and from the remaining ¾ of the solution there were isolated, in known manner, 98 kg of 2-methyl-5-nitroimidazole corresponding to about 70% of theoretical.

What is claimed is:

1. In a process for the production of 2-methyl-5-nitroimidazole which comprises treating 2-methylimidazole with a nitration mixture of nitric and sulphuric acids, cooling and reacting the mixture under reflux, an improvement which comprises adding to the reactants before the beginning of the nitration process a catalytic starting agent, consisting of an already reacted solution obtained by said nitration of 2-methylimidazole, whereby the induction period of the reaction is substantially shortened.

2. A process as claimed in claim 11 in which the 2-methylimidazole is first dissolved in said already reacted solution whereafter concentrated nitric acid is introduced, and finally sulphuric acid is gradually added until the nitration reaction commences.

* * * * *